United States Patent [19]

Metzner et al.

[11] Patent Number: 4,750,934
[45] Date of Patent: Jun. 14, 1988

[54] COMPOSITION OR CONCENTRATE FOR CONSERVING WOOD AND WOOD MATERIALS

[75] Inventors: Wolfgang Metzner; Volker Hellwig, both of Krefeld; Reiner Pospischil, Bergheim-Fliesteden; Siegfried Cymorek, Krefeld-Gartenstadt, all of Fed. Rep. of Germany

[73] Assignee: Desowag-Bayer Holzschutz GmbH, Duesseldorf, Fed. Rep. of Germany

[21] Appl. No.: 901,719

[22] Filed: Aug. 29, 1986

[30] Foreign Application Priority Data

Aug. 31, 1985 [DE] Fed. Rep. of Germany ....... 3531257

[51] Int. Cl.$^4$ .............................................. C01D 5/14
[52] U.S. Cl. ..................................................... 106/18
[58] Field of Search ............... 106/18.24, 18; 568/637; 560/9

[56] References Cited

U.S. PATENT DOCUMENTS

| | | | |
|---|---|---|---|
| 3,996,244 | 12/1976 | Fujimoto et al. | 560/9 |
| 4,261,920 | 4/1981 | Fuchs et al. | 568/637 |
| 4,547,366 | 10/1985 | Marx | 514/552 |

FOREIGN PATENT DOCUMENTS 0038932 11/1981 European Pat. Off. .
0149005 7/1985 European Pat. Off. .
2128091 4/1984 United Kingdom .

OTHER PUBLICATIONS

Abstract EP 43035.

*Primary Examiner*—Theodore Morris
*Attorney, Agent, or Firm*—Foley & Lardner, Schwartz, Jeffery, Schwaab, Mack, Blumenthal & Evans

[57] ABSTRACT

A composition or concentrate for preserving wood, which comprises 0.001–5% by weight of cyano-(4-fluoro-3-phenoxyphenyl)-methyl 3-(2,2-dichloroethenyl)-2,2-dimethylcyclopropanecarboxylate and/or (pentafluorophenyl)-methyl 1R, 3R-3-(2,2-dichloroethenyl)-2,2-dimethylcyclopropanecarboxylate or enantiomeric compounds thereof and more than 75% by weight, preferably more than 90% by weight, of a mixture comprising at least one binder at least one diluent, and optionally at least one emulsifier and/or wetting agent or mixture thereof. The binder in the wood preservative or concentrate (calculated as solids) amounts to at least 1% by weight, preferably at least 4% by weight of the composition. An alkyd resin and/or a vegetable drying oil is preferably used in the composition as the organic binder for preventing or reducing damage to beneficial insects.

24 Claims, 1 Drawing Sheet

TEST NO. 1

TEST NO. 2

TEST NO. 3

COMPOSITION OR CONCENTRATE FOR CONSERVING WOOD AND WOOD MATERIALS

BACKGROUND OF THE INVENTION

The present invention relates to a composition or concentrate for preserving wood and wood materials at least one insecticide or insecticide mixture, at least one solvent or solvent mixture, a binder or binder mixture and, optionally, a fungicide or fungicide mixture, processing aid and/or additive, dye, pigment, dye mixture or pigment mixture, in which the composition contains a defined proportion of specific insecticides or insecticide mixtures.

The chemical compounds 2,2-dimethyl-3-dichlorovinyl-cis/trans-cyclopropanecarboxylic acid α-cyano-3'-phenoxy-4'-fluorobenzyl ester or cyano-(4-fluoro-3-phenoxyphenyl)-methyl 3-(2,2-dichloroethenyl)-2,2-dimethylcyclopropanecarboxylate (C.A.) and (-)1R-trans-2,2-dimethyl-3-(2,2-dichlorovinyl)-cyclopropanecarboxylic acid pentafluorobenzyl ester or (pentafluorophenyl)-methyl 1R,3R-3-(2,2-dichloroethenyl)-2,2-dimethylcyclopropanecarboxylate (C.A.) or enantiomeric compounds thereof are already known as insecticides (cf. German Offenlegungsschrift No. 2,709,264).

These compounds are insecticides having high contact-insecticidal activity. If attempts are made to use these insecticides as wood preservatives with solvents or diluents, the result, for example at a concentration of 0.05% by weight, on contact of the beetle species Sitophilus granarius with the treated surface is a destruction quota of 100% after 5 hours. Since useful insects can thus also be killed or endangered by overflows from the treated surfaces or on contact with the treated surface, the use of these insecticides as wood preservatives has hitherto been avoided. Furthermore, there is the additional disadvantage that the said insecticides, namely pentafluorobenzyl 1R-trans-2,2-dimethyl-3-(2,2-dichlorovinyl)-cyclopropanecarboxylate or (pentafluorophenyl)-methyl 1R,3R-3-(2,2-dichloroethenyl)-2,2-dimethylcyclopropanecarboxylate, sometimes suffer a reduction in activity after aging and/or exposure to the weather.

SUMMARY OF THE INVENTION

The object of the invention is to avoid the above disadvantages and to provide wood preservatives (or concentrates thereof) of the most long lasting activity possible with the additional use of the insecticides 2,2-dimethyl-3-dichlorovinyl-cis/transcyclopropanecarboxylic acid α-cyano-3'-phenoxy-4'-fluorobenzyl ester or cyano-(4-fluoro-3-phenoxyphenyl)methyl 3-(2,2-dichloroethenyl)-2,2-dimethylcyclopropanecarboxylate (C.A.) and/or (-)1R-trans-2,2-dimethyl-3-(2,2-dichlorovinyl)-cyclopropanecarboxylic acid pentafluorobenzyl ester or (pentafluorophenyl)-methyl 1R,3R-3-(2,2-dichloroethenyl)-2,2-dimethylcyclopropanecarboxylate (C.A.) or enantiomers thereof.

These objects are achieved by providing a wood preserving composition comprising an admixture of at least one insecticide, at least one organic binder or fixing agent, and at least one diluent, wherein, said insecticide comprises from 0.001 to 5% by weight of said composition, said binder comprises at least 1% by weight of the composition calculated as a solid, and said diluent and binder together comprise at least 75% by weight of said composition, and wherein said insecticide comprises a compound selected from the group consisting of cyano-(4-fluoro-3-phenoxyphenyl)-methyl 3-(2,2-dichloroethenyl)-2,2-dimethylcyclopropanecarboxylate, (pentafluorophenyl)-methyl 1R,3R-3-(2,2-dichloroethenyl)-2,2-dimethylcyclopropanecarboxylate, and enantiomeric compounds thereof.

BRIEF DESCRIPTION OF THE DRAWINGS

The invention will be explained in further detail with reference to the accompanying drawings wherein.

DETAILED DESCRIPTION OF THE PREFERRED EMBODIMENTS

Figure 1:
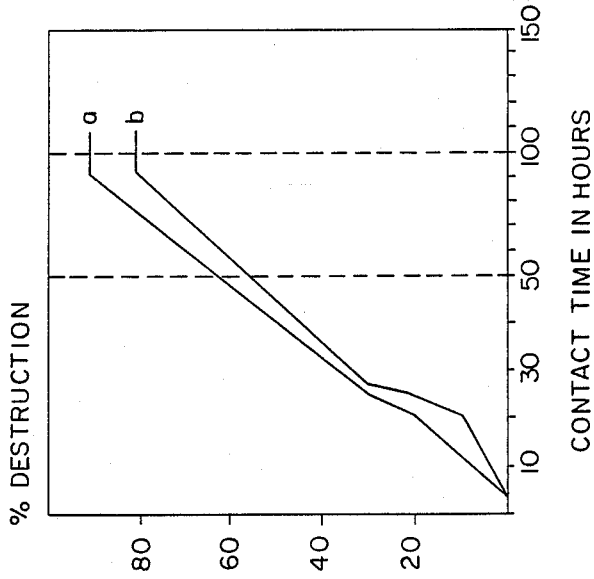
FIGS. 1 through 3 are graphs of a comparative test of the invention.
Figure 2:
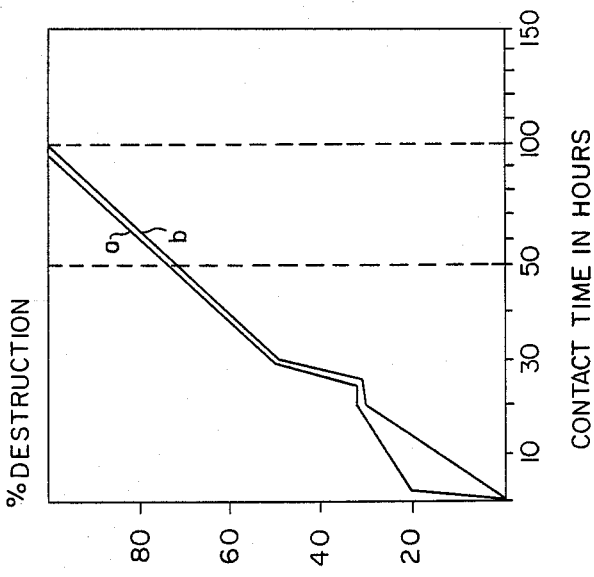
Figure 3:
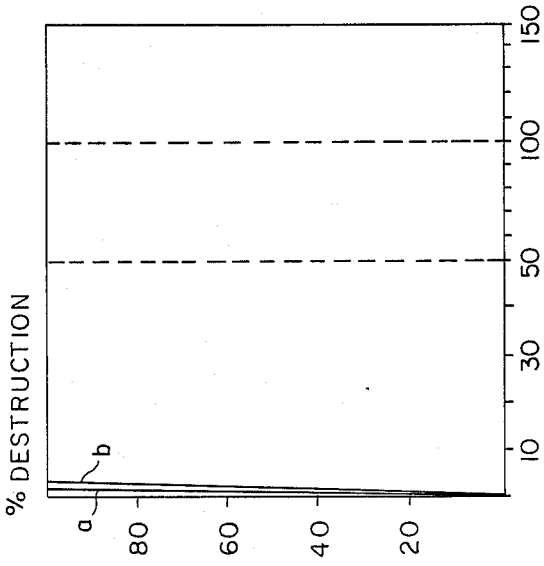

The invention relates to a composition or concentrate for preserving wood and wood materials, comprising at least one insecticide or insecticide mixture, at least one solvent or solvent mixture, a binder or binder mixture and, optionally, a fungicide, processing aid and/or additive, dye, pigment, or dye or pigment mixture, which composition or concentrate comprises 0.001–5% by weight of 2,2-dimethyl-3-dichlorovinyl-cis/trans-cyclopropanecarboxylic acid α-cyano-3'-phenoxy-4'-fluorobenzyl ester, which may be alternately described as cyano-(4-fluoro-3-phenoxyphenyl)-methyl 3-(2,2-dichloroethenyl)-2,2-dimethylcyclopropanecarboxylate (C.A.), and/or (-)1R-trans-2,2-dimethyl-3-(2,2-dichlorovinyl)cyclopropanecarboxylic acid pentafluorobenzyl ester, which may be alternately described as (pentafluorophenyl)-methyl 1R,3R-3-(2,2-dichloroethenyl)-2,2-dimethylcyclopropanecarboxylate (C.A.), or one of the enantiomers thereof and more than 75% by weight, preferably more than 90% by weight, of a mixture consisting of at least one binder and at least one diluent and/or at least one emulsifier and/or wetting agent or mixture thereof, with the proviso that the binder in the wood preservative or concentrate (calculated as a solid) amounts to at least 1% by weight, preferably more than 4% by weight.

The organic binders used within the scope of the present invention are the known synthetic resins and/or binding drying oils which are water-dilutable and/or soluble or dispersible or emulsifiable in the organic solvents used. In particular, binders comprising or containing acrylate resin, a vinyl resin, for example polyvinyl acetate, polyester resin, polycondensation resin or polyaddition resin, polyurethane resin, alkyd resin, silicone resin, vegetable drying oils and/or drying oils, and/or physically drying binders formed of a natural and/or synthetic resin.

In a particularly advantageous embodiment, the binder used is a synthetic resin in the form of an emulsion, dispersion or solution, preferably an alkyd resin or modified alkyd resin or a phenolic resin and/or hydrocarbon resin, preferably indene-coumarone resin. Bitumen or bituminous substances can also be used as binders in a quantity of up 10% by weight. Additionally, dyes, pigments, water-repellent agents, odor-correctives and inhibitors or corrosion inhibitors and the like can be employed.

According to the invention, the composition or concentrate preferably contains at least one alkyd resin and/or vegetable drying oil as the organic binder. Preferably, alkyd resins having an oil content of more than 45% by weight, most preferably 50–65% by weight, are used according to the invention.

The diluent comprises or consists of an organic solvent or solvent mixture, preferably an oily or oil-like organic solvent or solvent mixture having a low volatility or a mixture of water and/or at least one organic solvent, preferably at least one oily or oil-like organic solvent or solvent mixture having a low volatility, and at least one emulsifier and/or wetting agent.

Furthermore, the weight ratio of binder or binder mixture to the diluent or diluent mixture (including the constituents, such as solvent and/or water, contained in the diluent or diluent mixture and the emulsifier or emulsifier mixture and/or wetting agent or wetting agent mixture contained in the composition or concentrate) is from 8.5:1 to 1:99.

According to one embodiment, the organic binder or binder mixture may consist entirely, but preferably partially comprises, at least one fixing agent or at least one plasticizer.

In this case, the organic binder or binder mixture comprises from 1 to 75% by weight, preferably 0.01 to 35% by weight, (relative to 100% by weight of binder used, calculated as the solid) of at least one fixing agent or at least one plasticizer.

Useful fixing agents or plasticizers are primarily compounds which, in addition to a certain bonding or adhesion to the active compound, are additionally intended to prevent volatilization of the active compounds and/or crystallization or precipitation. Preferably used compounds include:

(a) plasticizers, for example alkyl, aryl or aralkyl phthalates, preferably dibutyl, dioctyl and benzyl butyl phthalates, alkyl phosphates or phosphoric acid esters, preferably tributyl phosphate, adipates, preferably di-(2-ethylhexyl) adipate, stearates and oleates, for example alkyl stearates or alkyl oleates, preferably butyl oleate, butyl stearate or amyl stearate, bis-(dimethylbenzyl) ether, ethyl p-toluenesulfonate, glycerol esters, glycerol ethers or higher-molecular weight glycol ethers, and/or (b) fixing agents based on ketones and/or polyvinyl alkyl ethers, for example ketones with alkyl, aryl or aralkyl groups, preferably benzophenone or ethylbenzophenone, and polyvinyl alkyl ethers, preferably polyvinyl methyl ether.

The organic solvents employed are preferably polar organic solvents and/or oily or oil-like solvents having a low volatility with an evaporation number above 35 and a flash point above 30° C., preferably about 45° C. Appropriate mineral oils or their aromatic fractions or mineral oil-containing solvent mixtures, preferably solvent naphtha, petroleum and/or alkylbenzene and the like, are used as such water-insoluble, oily or oil-like low volatility solvents. According to a preferred embodiment, tetramethylbenzenes are used, particularly aromatic solvent mixtures containing more than 60% by weight, preferably more than 75% by weight, tetramethylbenzene.

Mineral oils having a boiling range of 117°–220° C., solvent naphtha having a boiling range of 170°–220° C., spindle oil having a boiling range of 250°–350° C., petroleum or aromatics of boiling range 160°–280° C., turpentine oil and the like may advantageously be used.

In one embodiment, liquid aliphatic hydrocarbons having a boiling range of from 180° to 210° C. or high-boiling mixtures of aromatic and aliphatic hydrocarbons having a boiling range of from 180° to about 220° C. and/or spindle oil and/or monochloronaphthalene, preferably α-monochloronaphthalene, may also be used.

The oily or oil-like organic solvents having a low volatility with an evaporation number above 35 and flash point have 30° C., preferably above 45° C., can be partially replaced by organic solvents having high or medium volatility, provided that the overall solvent mixture still has an evaporation number above 35 and a flash point above 30° C., preferably above 45° C., and that the insecticide/fungicide mixture is soluble or emulsifiable in the solvent mixture.

Preferred polar organic solvents or solvent mixtures are those containing hydroxyl groups, ether groups, keto groups and/or ester groups. Preferably, glycol ethers, diacetone alcohol, or water-soluble polyols or their esters are employed.

According to a preferred embodiment, the ready to use wood preserving composition comprises 0.001–1% by weight, preferably 0.005–0.2% by weight, of cyano-(4-fluoro-3-phenoxyphenyl)-methyl 3-(2,2-dichloroethenyl)-2,2-dimethylcyclopropanecarboxylate and/or (pentafluorophenyl)-methyl 1R,3R-3-(2,2-dichloroethenyl)-2,2-dimethylcyclopropanecarboxylate or enantiomeric compounds thereof and 1–40%, preferably 4–33%, by weight (calculated as the solid) of at least one organic binder and/or fixing agent or plasticizer. The weight ratio of the total content of organic binder and/or fixing agent or plasticizer to the total content of diluent (including solvent or solvent mixture and/or water and/or emulsifier and/or wetting agent) is 1:1.2 to 1:99, preferably 1:2 to 1:25.

In particular, ready to use composition may comprise 0.001 to 1% by weight, preferably 0.005 to 0.2% by weight, of cyano-(4-fluoro-3-phenoxyphenyl)-methyl 3-(2,2-dichloroethenyl)-2,2-dimethylcyclopropanecarboxylate and/or (pentafluoro-phenyl)-methyl 1R,3R-3-(2,2-dichloroethenyl)-2,2-dimethylcyclopropane-carboxylate or enantiomeric compounds thereof and 1 to 40% by weight, preferably 4 to 33% by weight, of at least one organic binder and/or fixing agent or plasticizer, 0 to 7% by weight, preferably 0.5 to 5% by weight, of a fungicide or fungicide mixture soluble in the organic solvent or solvent mixture, 0 to 8% by weight, preferably 0.1 to 4% by weight, of at least one water-soluble and/or water-insoluble dye, colored pigment and/or corrosion inhibitor, drying agent and/or UV-stabilizer, and from 98.999% by weight to 44% by weight, preferably from 95.395% by weight to 57.8% by weight, of a diluent or diluent mixture consisting of at least one organic solvent or solvent mixture and/or water and/or at least one emulsifier and/or wetting agent or mixture thereof.

The concentrate, according to the invention, for preserving wood and wood materials comprises 0.002 to 5% by weight, preferably 0.003 to 2% by weight, of cyano-(4-fluoro-3-phenoxyphenyl)-methyl 3-(2,2-dichloroethenyl)-2,2-dimethylcyclopropanecarboxylate and/or (pentafluorophenyl)-methyl 1R,3R-3-(2,2-dichloroethenyl)-2,2-dimethylcyclopropanecarboxylate or enantiomeric compounds thereof and 2 to 85% by weight, preferably 8 to 40% by weight, (calculated as the solid) of at least one organic binder and/or fixing agent or plasticizer, the weight ratio of the total content of organic binder and/or fixing agent or plasticizer to the total content of diluent (including solvent or solvent mixture and/or water and/or emulsifier and/or wetting agent) being 8.5 : 1 to 1 : 48, preferably 1:1.45 to 1:11.5.

In particular, the concentrate may comprise 0.002 to 5% by weight, preferably 0.003 to 2% by weight, of cyano-(4-fluoro-3-phenoxyphenyl)-methyl 3-(2,2-dichloroethenyl)-2,2-dimethylcyclopropanecarboxylate and/or (pentafluorophenyl)-methyl 1R,3R-3-(2,2-dichloroethenyl)-2,2-dimethylcyclopropanecarboxylate or enantiomeric compounds thereof and 2 to 85% by weight, preferably 8 to 60% by weight, of at least one organic binder and/or fixing agent or plasticizer, 0 to 20% by weight, preferably 1 to 8% by weight, of a fungicide or fungicide mixture soluble in the organic solvent or solvent mixture and a diluent or diluent mixture as the remainder, consisting of at least one organic solvent or solvent mixture, or water and an organic chemical solvent or solvent mixture and/or at least one emulsifier and/or wetting agent or a mixture thereof and, optionally dyes, colored pigments, corrosion inhibitors, drying agents and/or UV-stabilizers.

According to a preferred embodiment the concentrate contains as the emulsifier or emulsifier mixture, at least one ethoxylated phenol containing a side group, preferably an ethoxylated (10)-nonylphenol and/or an ethoxylated fatty acid and/or polyalkylene glycol ether. The emulsifiers can also be combined with wetting agents, for example with wetting agents based on organic phosphorus/amine compounds.

According to another embodiment, the concentrate and the agent, prepared therefrom, for preserving wood and wood materials may contain a mixture of emulsifiers of different chain lengths, of which at least one emulsifier has an ethoxylated side chain of fewer than 10 ethoxy groups and of which at least one other emulsifier has an ethoxylated side chain of more than 10 ethoxy groups.

According to a particularly advantageous embodiment, the concentrate contains, as the water-dilutable synthetic resin, an alkyd resin of medium oil length. In spite of the low proportion of organic solvent, for example based on petroleum, the use of this synthetic resin has the result that, on the other hand, better fixing of the active compounds is achieved and, on the other hand, film formation is made possible, depending on the synthetic resin content.

According to one embodiment, the concentrate contains one or more compounds having an alkaline reaction, as a buffer material or pH value regulator to produce a pH value of 7 to 10.

Preferred non-ionic organic water-insoluble fungicides or water-insoluble fungicide mixtures comprise tetravalent organo-tin compounds or (N-cyclohexyl-diazeniumdioxy)-metal compounds (or salts of N-nitroso-N-cyclohexylhydroxylamine), preferably the aluminum compound thereof, pentachloro-phenol,2,5-dimethyl-N-cyclohexyl-N-methoxy-furan-3-carboxamide and/or N,N-dimethyl-N'-(fluorodichloromethyl-thio)sulfamine and/or N,N-dimethyl-N'-p-tolyl-N'-(dichlorofluoro-methylthio)-sulfamide, or of two or more of these compounds.

Examples of suitable oil-soluble tetravalent, fungicidal organo-tin compounds include: tributyl-tin benzoate, tributyl tin oleate, tris-(tributyl-tin) phosphate, bis-(tributyl-tin) oxide, tributyl-tin naphthenate and tributyl-tin octoate.

According to another embodiment, the non-ionic fungicides may also be wholly or partially replaced by ionic fungicides, preferably fungicidal quaternary ammonium compounds or potassium salts of N-nitroso-N-cyclohexyl-hydroxylamine. Dialkyl($C_{10}$–$C_{18}$)-alkyl(-$C_1$–$C_5$)-benzylammonium halides and/or alkyl($C_{10}$–$C_{18}$)dialkyl($C_1$–$C_5$)-benzylammonium halides may be employed as quaternary fungicidal ammonium compounds.

In a preferred embodiment for the preparation of emulsion concentrates or water-containing wood preservatives, the organic solvents are, mixed with polar solvents, preferably solvents or solubilizers containing hydroxyl or ether groups.

Suitable organic polar solvents are those which contain hydroxyl groups and/or ether groups and/or keto groups. Ethylene glycol (2-hydroxyethanol), diethylene glycol (2,2-dihydroxy-diethyl ether), ethylglycol (2-hydroxy-diethyl ether), butylglycol (1-hydroxy-2-n-butoxyethane) and/or ethyldiglycol (2-hydroxy-2-ethoxy-diethyl ether) and/or diacetone alcohol are examples of preferred organic solvents containing hydroxyl groups and/or ether groups and/or keto groups.

For certain formulations, it can be advantageous to add antifoam agents such as silicone antifoam agents or alkyl phosphates, preferably n-butyl phosphate. In addition, dyes or other additives, for example UV-stabilizers, thickeners, drying agents, corrosion inhibitors and the like, may be added, depending on the desired properties of the composition. Preferred drying agents, which preferably are employed in combination with a binder based on a vegetable oil, include octoates and/or naphthenates of cobalt, zinc, cerium and/or manganese.

As diluents for the preparation of ready-to-use compositions from concentrates, the same diluents or diluent mixtures described above may be used, optionally in combination with binders, additives, processing aids, dyes, colored pigments, UV-stabilizers, corrosion inhibitors and the like.

The wood preservative compositions of the invention can be applied to wood by known methods, preferably by brushing, squirting, spraying or using impregnation methods, such as dipping, pressure and/or vacuum methods.

The invention also relates to a process for the preparation of a wood preservative concentrate and to compositions prepared from such concentrates for preserving wood and wood materials. According to this process, the insecticide and/or fungicide soluble in the organic solvent or solvent mixture, and the non-ionic emulsifier or non-ionic emulsifier mixture are treated at temperatures of 10° to 80° C., preferably 30° to 60° C., and at pressures of 400 mm Hg to 850 mm Hg (0.5332 to 1,1332 bar or 533.2 to 1133.2 hectopascal), preferably 600 mm Hg to 790 mm Hg (0.7999 to 1.0532 bar or 799.9 to 1053.2 hectopascal) in the presence or absence of the other substances or constituents of these substances, until a solution is formed, the remaining substances and, optionally, water being added afterwards to the solution.

The emulsifiers or surfactants may be known emulsifiers or surfactants. The surfactant or surfactant mixture may consist, for example, of isopropylamine dodecylbenzenesulfonate, polyoxyethylenesorbitan oleate/laurate and/or sorbitol oleate/laurate, polyoxyethylene(30)-nonylphenol and/or polyalkylglycol ethers or esters and/or isopropylamine dodecylbenzenesulfonate and/or Ca-alkylarylsulfonate.

The surfactant or surfactant mixture preferably contains at least one alkylarylsulfonate, a derivative of an alkylarylsulfonic acid and/or a polyoxyethylene derivative and/or a polyalkylene glycol ether or ester or polyalkylglycol ether or ester, and/or a surface-active organic compound containing one or more polyoxyethylene groups and/or one or more fatty acid groups.

EXAMPLES

The invention will be illustrated in further detail by the follow examples, which are not, however, to be considered as limiting the scope of the invention. All percentages are percent by weight unless otherwise indicated.

EXAMPLE 1

Impregnating paint (oily paint with insecticidal/termiticidal and fungicidal properties)
0.15% cyano-(4-fluoro-3-phenoxyphenyl)-methyl 3-(2,2-dichloroethenyl)-2,2-dimethylcyclopropanecarboxylate (Cyfluthrin)
0.60% N,N-dimethyl-N'-(fluorodichloromethylthio)-sulfamide
2.00% 2,5-dimethyl-N-cyclohexyl-N-methoxy-furan-3-carboxamide
5.00% alkyd resin (calculated as solids), having an acid number of 9 an oil content of 65%, and a viscosity of 3500 mpa s at 60% in solvent naphtha 60), and
92.25% aliphatic and aromatic solvents, preferably more than 60% by weight (relative to 100% by weight of solvent mixture) of tetramethylbenzene(s) and less than 40% by weight of aliphatic solvent (boiling range 180°–210° C., flash point 59° C., solubility parameter 7.6)

EXAMPLE 2

Concentrate for producing ready-to-use impregnating agents according to Example 1.
0.60% cyano-(4-fluoro-3-phenoxyphenyl)-methyl 3-(2,2-dichloroethenyl)-2,2-dimethylcyclopropanecarboxylate (Cyfluthrin)
2.40% N,N-dimethyl-N'-(fluorodichloromethylthio)-sulfamide
8.00% 2,5-dimethyl-N-cyclohexyl-N-methoxy-furan-3-carboxamide
20.00% alkyd resin (calculated as solids) having an acid number of 9, an oil content of 65%, and a viscosity of 3500 mpa s at 60% in solvent naphtha 60, and
69.00% aromatic solvents predominantly containing tetramethylbenzene(s)

EXAMPLE 3

Aqueous impregnation composition with insecticidal/termiticidal and fungicidal properties
0.15% cyano-(4-fluoro-3-phenoxyphenyl)-methyl 3-(2,2-dichloroethenyl)-2,2-dimethylcyclopropanecarboxylate (Cyfluthrin)
1.00% 2,5-dimethyl-N-cyclohexyl-N-methoxy-furan-3-carboxamide
2.40% alkyd resin (calculated as solids), having an oil content of 50%, an acid number of 48, and a viscosity of 2300 mpa s at 70% in butylglycol
3.00% emulsifier mixture consisting of ethoxylated (10)-nonylphenol polyalkylene glycol ether
1.45% aliphatic and aromatic solvents
2.00% butylglycol, and
90.00% of water

EXAMPLE 4

Concentrate for aqueous impregnation composition
1.50% cyano-(4-fluoro-3-phenoxyphenyl)-methyl 3-(2,2-dichloroethenyl)-2,2-dimethylcyclopropanecarboxylate (Cyfluthrin)
10.00% 2,5-dimethyl-N-cyclohexyl-N-methoxy-furan-3-carboxamide
14.50% aromatic and aliphatic solvents, preferably a solvent naphtha mixture (boiling range 180°–210° C., flash point 59° C., solubility parameter 7.6) and/or a tetramethylbenzene mixture (boiling range 180°–210° C., flash point 59° C., solubility parameter 7.6)
24.00% alkyd resin (calculated as solids)
20.00% butylglycol, and
30.00% emulsifier, preferably ethoxylated (10)nonylphenol

EXAMPLE 5

Pigmented protective wood varnish (oily varnish with insecticidal/termiticidal and fungicidal properties)
0.15% (pentafluorophenyl)-methyl 1R,3R-3-(2,2-dichloroethenyl)-2,2-dimethylcyclopropanecarboxylate (Fenfluthrin)
0.60% N,N-dimethyl-N'-(fluorodichloromethylthio)-sulfamide
2.00% 2,5-dimethyl-N-cyclohexyl-N-methoxy-furan-3-carboxamide
20.00% alkyd resin (calculated as solids), having an acid number of 9, an oil content of 65%, and a viscosity of 3500 mpa s at 60% in solvent naphtha 60
2.00% yellow iron oxide pigment
0.30% red iron oxide pigment
0.20% wetting agent mixture, preferably consisting of or comprising organic phosphorus/amine compounds
0.10% drying agent (cobalt octoate)
0.50% thickener (montmorillonite)
74.15% aliphatic and aromatic solvents, preferably consisting of more than 60% by weight (relative to 100% by weight of the solvent mixture) of tetramethylbenzene(s) and less than 40% by weight of aliphatic solvent (boiling range 180°–210° C., flash point 59° C., solubility parameter 7.6)

EXAMPLE 6

Wood preservative primer
0.1% cyano-(4-fluoro-3-phenoxyphenyl)-methyl 3-(2,2-dichloroethenyl)-2,2-dimethylcyclopropanecarboxylate
10.0% alkyd resin (calculated as solids), having an acid number of 9, an oil content of 65%, and a viscosity of 3500 mpa s at 60% in solvent naphtha 60
0.1% drying agent
89.8% water-insoluble, aromatic organic solvent mixture

EXAMPLE 7

0.1% cyano-(4-fluoro-3-phenoxyphenyl)-methyl 3-(2,2-dichloroethenyl)-2,2-dimethylcyclopropanecarboxylate (Cyfluthrin)
0.05% (pentafluorophenyl)-methyl 1R,3R-3-(2,2-dichloroethenyl)-2,2-dimethylcyclopropanecarboxylate (Fenfluthrin)
0.60% N,N-dimethyl-N'-(fluorodichloromethylthio)-sulfamide
2.00% 2,5-dimethyl-N-cyclohexyl-N-methoxy-furan-3-carboxamide
20.00% alkyd resin (calculated as solids), having an acid number of 9, an oil content of 65%, and a viscosity of 3500 mpa s at 60% in solvent naphtha 60
2.00% yellow iron oxide pigment
0.30% red iron oxide pigment 0.20% wetting agent mixture, preferably consisting of or comprising organic phosphorus/amine compounds
0.10% drying agent (cobalt octoate)
0.50% thickener (montmorillonite)
74.15% aliphatic and aromatic solvents, preferably consisting of more than 60% by weight (relative to 100% by weight of solvent mixture) of tetramethylbenzene(s) and less than 40% by weight of aliphatic solvent (boiling range 180°–210° C., flash point 59° C., solubility parameter 7.6)

COMPARATIVE TEST:

To determine the influence of the binder content in wood preserving compositions when cyano-(4-fluoro-3-phenoxyphenyl)-methyl 3-(2,2-dichloroethenyl)-2,2-dimethylcyclopropanecarboxylate is used, the following comparative test was carried out. The test is intended to demonstrate that beneficial arthropods are not attacked by a wood preserving composition according to the invention, whereas destruction of the beneficial insects occurred when only aromatic solvents (for example toluene) were used for wood-preserving impregnation. Cyano-(4-fluoro-3-phenoxyphenyl)-methyl 3-(2,2-dichloroethenyl)-2,2-dimethylcyclopropanecarboxylate was used in comparative tests 1 and 2 in 0.1% concentration, the comparative test being based on the following composition:

1. Cyano-(4-fluoro-3-phenoxyphenyl)-methyl 3-(2,2-dichloroethenyl)-2,2-dimethylcyclopropanecarboxylate in 0.1% concentration in toluene (without binder)—see graph of Test No. 1.

2. A wood preservative according to Example 6, with 0.1% concentration of cyano-(4-fluoro-3-phenoxyphenyl)-methyl 3-(2,2-dichloroethenyl)-2,2-dimethylcyclopropanecarboxylate —see graph of Test No. 2.

3. A comparison with untreated control samples (graph of Test No. 3), see attached illustrations of Tests 1 through 3.

The test animal selected was the ground beetle species (Carabidae) Trechus quadristriatus (Schrk.), a species which is one of the most abundant ground beetle species in central Europe and which has already been used in ecological tests of plant protective agents.

On test woods treated with 0.1% of cyano-(4-fluoro-3-phenoxyphenyl)-methyl 3-(2,2-dichloroethenyl)-2,2-dimethylcyclopropanecarboxylate in toluene, the test animals were killed in less than 3 hours (Test No. 1).

When the wood was primed with a wood preservative according to Example 6 (Test No. 2), the active compound cyano-(4-fluoro-3-phenoxyphenyl)-methyl 3-(2,2-dichloroethenyl)-2,2-dimethylcyclopropanecarboxylate had virtually no influence on the test animals. When using the wood preservative formulation according to the invention, beneficial insects (for example arthropods), which come into contact with the treated surface but do not gnaw at it, are not attacked.

Two test runs designated a) and b) are reproduced in each of the graphs of Nos. 1 through 3.

What is claimed is:

1. A wood preserving composition comprising an admixture of at least one insecticide, at least one organic binder comprising a material selected from the group consisting of alkyd resins and vegetable drying oils, and at least one diluent, wherein said insecticide comprises from 0.001 to 5% by weight of said composition, said binder comprises at least 1% by weight of the composition calculated as a solid, and said diluent and binder together comprise at least 75% by weight of said composition, the weight ratio of binder to diluent being from 8.5:1 to 1:99, and wherein said insecticide comprises a compound selected from the group consisting of cyano-(4-fluoro-3-phenoxyphenyl)-methyl 3-(2,2-dichloroethenyl)-2,2-dimethylcyclopropanecarboxylate, (pentafluorophenyl)-methyl 1R,3R-3-(2,2-dichloroethenyl)-2,2-dimethylcyclopropanecarboxylate, and enantiomeric compounds thereof, said composition, when applied to wood, killing insects which attack the wood but not killing insects which otherwise come in contact with the wood.

2. A wood preserving composition according to claim 1, wherein said binder comprises at least 4% by weight of said composition calculated as a solid, and said binder and diluent together comprise at least 90% by weight of said composition.

3. A wood preserving composition according to claim 1, wherein said admixture further comprises at least one fungicide.

4. A wood preserving composition according to claim 1, further comprising at least one additional ingredient selected from the group consisting of processing aids, dyes and pigments.

5. A wood preserving composition according to claim 1, wherein said composition is a concentrate intended to be diluted before use.

6. A wood preserving composition according to claim 1, wherein said diluent is an organic solvent.

7. A wood preserving composition according to claim 6, wherein said organic solvent is a polar organic solvent.

8. A wood preserving composition according to claim 6, wherein said organic solvent is a low volatility organic oil.

9. A wood preserving composition according to claim 1, wherein said diluent is a mixture of water, at least one organic solvent, and at least one emulsifier or wetting agent.

10. A wood preserving composition according to claim 9, wherein said organic solvent is a polar organic solvent.

11. A wood preserving composition according to claim 9, wherein said organic solvent is a low volatility organic oil.

12. A wood preserving composition according to claim 1, wherein said binder comprises at least one material selected from the group consisting of fixing agents and plasticizers.

13. A wood preserving composition according to claim 12, wherein said binder comprises up to 75% by weight of a material selected from the group consisting of fixing agents and plasticizers.

14. A wood preserving composition according to claim 13, wherein said binder comprises from 0.01 to 35% by weight of a material selected from the group consisting of fixing agents and plasticizers.

15. A ready to use wood preserving composition according to claim 1, comprising from 0.001 to 1% by weight of an insecticide selected from the group consisting of cyano-(4-fluoro-3-phenoxyphenyl)methyl 3-(2,2-dichloroethenyl)-2,2-dimethylcyclopropanecarboxylate, (pentafluorophenyl)methyl 1R,3R-3-(2,2-dichloroethenyl)-2,2-dimethylcyclopropanecarboxylate, and enantiomeric compounds thereof, and from 1 to 40% by weight calculated as a solid of organic binder, and wherein the weight ratio of binder to diluent is from 1:1.2 to 1:99.

16. A ready to use wood preserving composition according to claim 15, comprising from 0.005 to 0.2% by weight of an insecticide selected from the group consisting of cyano-(4-fluoro-3-phenoxyphenyl)methyl 3-(2,2-dichloroethenyl)-2,2-dimethylcyclopropanecarboxylate, (pentafluorophenyl)methyl 1R,3R-3-(2,2-dichloroethenyl)-2,2-dimethylcyclopropanecarboxylate, and enantiomeric compounds thereof, and from 4 to 33% by weight calculated as solids of organic binder, and wherein the weight ratio of binder to diluent is from 1:2 to 1:25.

17. A ready to use wood preserving composition according to claim 15, comprising from 0.001 to 1% by weight of at least one insecticide selected from the group consisting of cyano-(4-fluoro-3-phenoxyphenyl)methyl 3-(2,2-dichloroethenyl)-2,2-dimethylcyclopropanecarboxylate, (pentafluorophenyl)methyl 1R,3R-3-(2,2-dichloroethenyl)-2,2-dimethylcyclopropanecarboxylate, and enantiomeric compounds thereof, from 1 to 40% by weight calculated as solids of organic binder, from 0 to 7% by weight of at least one fungicide soluble in said diluent, from 0 to 8% by weight of at least one material selected from the group consisting of dyes, colored pigments, drying agents and ultraviolet stabilizers, and from 98.999 to 44% by weight of diluent.

18. A ready to use wood preserving composition according to claim 17, wherein said diluent comprises at least one material selected from the group consisting of organic solvents, water, and emulsifiers or wetting agents.

19. A ready to use wood preserving composition according to claim 17, comprising from 0.005 to 0.2% by weight of at least one insecticide selected from the group consisting of cyano-(4-fluoro-3-phenoxyphenyl)methyl 3-(2,2-dichloroethenyl)-2,2,-dimethylcyclopropanecarboxylate, (pentafluorophenyl)methyl 1R,3R-3-(2,2-dichloroethenyl)-2,2-dimethylcyclopropanecarboxylate, and enantiomeric compounds thereof, from 4 to 33% by weight calculated as solids of organic binder, from 0.5 to 5% by weight of at least one fungicide soluble in said diluent, from 0.1 to 4% by weight of at least one material selected from the group consisting of dyes, colored pigments, drying agents and ultraviolet stabilizers, and from 95.395 to 57.8% by weight of diluent.

20. A concentrate for a wood preserving composition according to claim 1, comprising from 0.002 to 5% by weight of an insecticide selected from the group consisting of cyano-(4-fluoro-3-phenoxyphenyl)methyl 3-(2,2-dichloroethenyl)-2,2-dimethylcyclopropanecarboxylate, (pentafluorophenyl)methyl 1R,3R-3-(2,2-dichloroethenyl)-2,2-dimethylcyclopropanecarboxylate, and enantiomeric compounds thereof, and from 2 to 85% by weight calculated as solids of organic binder, and wherein the weight ratio of organic binder to diluent is from 8.5:1 to 1:48.

21. A concentrate for a wood preserving composition according to claim 1, comprising from 0.002 to 5% by weight of at least one insecticide selected from the group consisting of cyano-(4-fluoro-3-phenoxyphenyl)methyl 3-(2,2-dichloroethenyl)-2,2-dimethylcyclopropanecarboxylate, (pentafluorophenyl)methyl 1R,3R-3-(2,2-dichloroethenyl)-2,2-dimethylcyclopropanecarboxylate, and enantiomeric compounds thereof, from 2 to 85% by weight calculated as solids of organic binder, from 0 to 20% by weight of fungicide soluble in said diluent, and the remainder comprising diluent.

22. A concentrate for a wood preserving composition according to claim 21, wherein said diluent comprises at least one material selected from the group consisting of organic solvents, water, and emulsifiers or wetting agents.

23. A concentrate for a wood preserving composition according to claim 21, further comprising at least one material selected from the group consisting of dyes, colored pigments, corrosion inhibitors, drying agents, and ultraviolet stabilizers.

24. A concentrate for a wood preserving composition according to claim 21, comprising from 0.003 to 3% by weight of at least one insecticide selected from the group consisting of cyano-(4-fluoro-3-phenoxyphenyl)methyl 3-(2,2-dichloroethenyl)-2,2-dimethylcyclopropanecarboxylate, (pentafluorophenyl)methyl 1R,3R-3-(2,2-dichloroethenyl)-2,2-dimethylcyclopropanecarboxylate, and enantiomeric compounds thereof, from 8 to 60% by weight calculated as solids of organic binder, from 1 to 8% by weight of fungicide soluble in said diluent, and the remainder comprising diluent.

* * * * *